US007955863B2

(12) United States Patent
Cox

(10) Patent No.: US 7,955,863 B2
(45) Date of Patent: Jun. 7, 2011

(54) MICROFLUIDIC DEVICE AND MATERIAL MANIPULATING METHOD USING SAME

(75) Inventor: David Cox, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 367 days.

(21) Appl. No.: 12/028,887

(22) Filed: Feb. 11, 2008

(65) Prior Publication Data

US 2008/0142455 A1 Jun. 19, 2008

Related U.S. Application Data

(62) Division of application No. 10/730,870, filed on Dec. 8, 2003, now Pat. No. 7,329,391.

(51) Int. Cl.
*G01N 15/06* (2006.01)
*G01N 33/00* (2006.01)
*G01N 33/48* (2006.01)

(52) U.S. Cl. ........... 436/177; 422/50; 422/68.1; 422/81; 422/82; 422/100; 436/43; 436/47; 436/174; 436/178; 436/180

(58) Field of Classification Search .................. 422/100, 422/101; 436/43, 174, 180, 177, 178
See application file for complete search history.

(56) References Cited

U.S. PATENT DOCUMENTS

| | | | | |
|---|---|---|---|---|
| 5,160,702 | A | 11/1992 | Kopf-Sill et al. | |
| 5,858,195 | A | 1/1999 | Ramsey | |
| 6,306,590 | B1 | 10/2001 | Mehta et al. | |
| 6,653,625 | B2 | 11/2003 | Andersson et al. | |
| 6,919,009 | B2 * | 7/2005 | Stonas et al. | 205/74 |
| 6,985,672 | B2 | 1/2006 | Kylberg et al. | |
| 7,329,391 | B2 | 2/2008 | Cox | |
| 2001/0046453 | A1 | 11/2001 | Weigl et al. | |
| 2002/0056816 | A1 | 5/2002 | Stark | |
| 2002/0104762 | A1 | 8/2002 | Stonas et al. | |
| 2002/0142480 | A1 | 10/2002 | Natan | |
| 2002/0146745 | A1 | 10/2002 | Natan et al. | |
| 2002/0158195 | A1 * | 10/2002 | Andersson et al. | 250/288 |
| 2003/0027150 | A1 | 2/2003 | Katz | |
| 2003/0036204 | A1 | 2/2003 | Stark et al. | |
| 2003/0119207 | A1 | 6/2003 | Dejneka et al. | |

FOREIGN PATENT DOCUMENTS

| | | |
|---|---|---|
| WO | WO 98/13684 | 4/1998 |
| WO | WO 02/41997 A1 | 5/2002 |

OTHER PUBLICATIONS

International Search Report, mailed Mar. 31, 2005, for International Application No. PCT/US2004/040024 (4 pages).

* cited by examiner

*Primary Examiner* — Brian J Sines
(74) *Attorney, Agent, or Firm* — Applied Biosystems, LLC; Jason Novak

(57) ABSTRACT

Microfluidic devices for manipulating relatively dense materials, such as colloidal rod particles, are provided. Microfluidic devices for separating a denser first material from a less-dense second material are provided. Methods of manipulating a relatively dense first material, for example, colloidal rod particles, and separating the first material from a less-dense second material, are provided. Methods of marking samples or sample components with relatively dense materials, are also provided.

17 Claims, 9 Drawing Sheets

Fig. 3b.
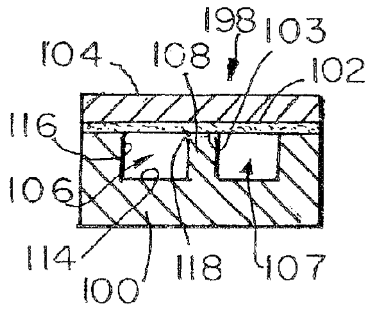
Fig. 4b.
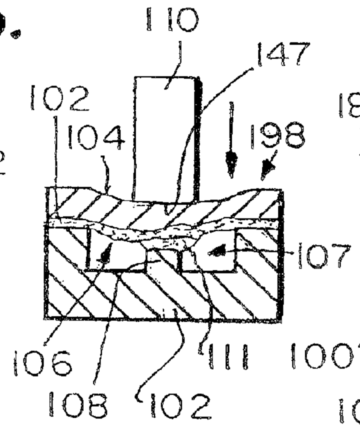
Fig. 5b.
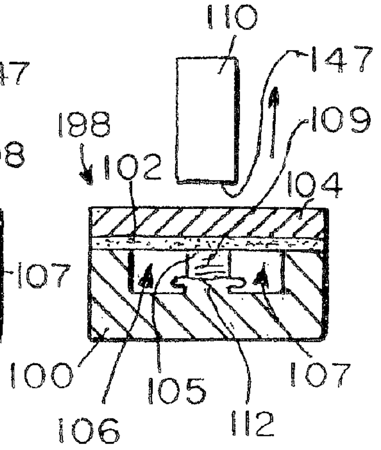
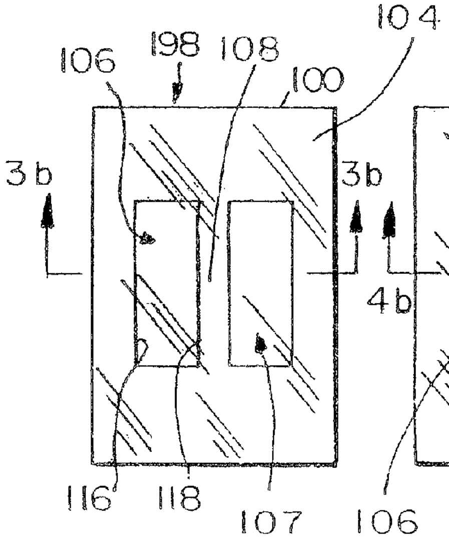
Fig. 3a.
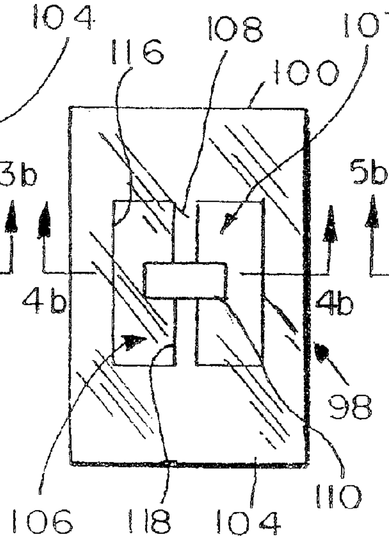
Fig. 4a.
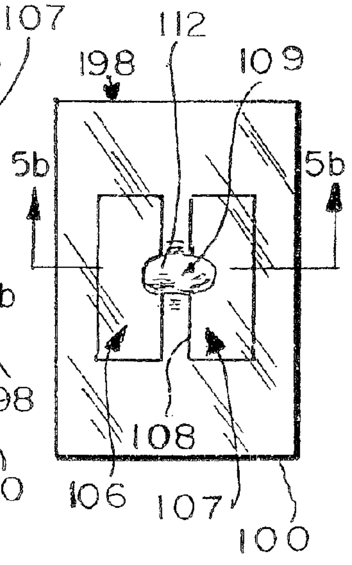
Fig. 5a.

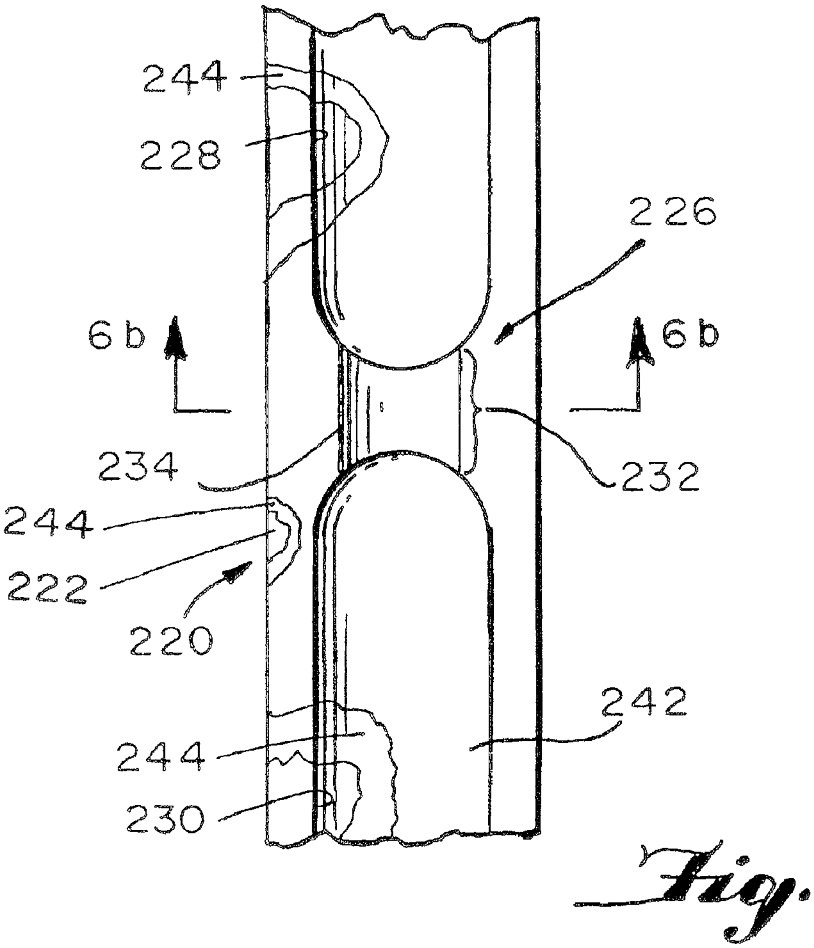
Fig. 6a.
Fig. 6b.
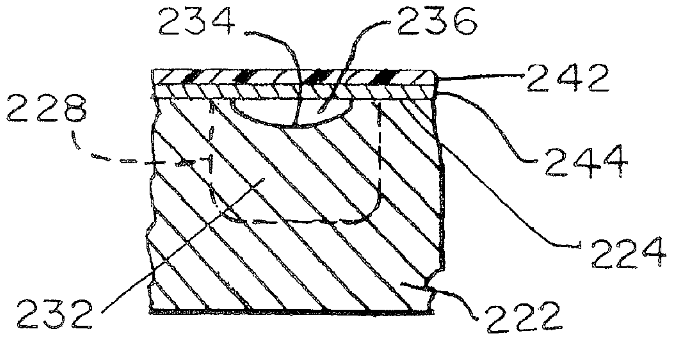

MICROFLUIDIC DEVICE AND MATERIAL MANIPULATING METHOD USING SAME

CROSS-REFERENCE TO RELATED APPLICATIONS

This application is a divisional of U.S. patent application Ser. No. 10/730,870 filed on Dec. 8, 2003 (Now U.S. Pat. No. 7,329,391, issued Feb. 12, 2008), which is incorporated herein in its entirety by reference.

FIELD

The present teachings relate to devices for and methods of separating materials from one another. The present teachings also relate to methods of labeling samples with identifiable markers and devices to carry out such methods.

BACKGROUND

In processing samples there sometimes arises a need to separate one or more components of the sample from one or more other components of the sample. A need exists for a device to carry out such a separation. Modern laboratories process many hundreds of samples on a regular basis. For this reason, distinct, different markers can be added to respective samples to label each with a unique identifier. However, manually marking samples can be laborious and time-consuming. A need also exists for a device that facilitates an efficient marking method.

SUMMARY

According to various embodiments, a microfluidic device is provided that can be used to separate a denser first material from a less-dense second material, by using centripetal force. The microfluidic device can include a processing pathway that includes a separation chamber. The separation chamber can include first and second inlets, an outlet, and a separation region disposed between the inlets and the outlet and radially outwardly of the inlets and outlets with respect to an axis of rotation about which the microfluidic device spins in operation. After applying a centripetal force to effect a separation of components, for example, by spinning the device, the less-dense second material can then be removed from the microfluidic device while leaving the denser first material in the microfluidic device. Exemplary materials that can be separated from a sample or mixture using the microfluidic device and method described herein can include an identifiable marker, a purification material, ion exchange beads, ion exchange resins, a grease, a resin, or other treatment particles or materials that can be separated from remaining components of a sample or mixture, for example, from remaining components of a liquid sample, an aqueous biological sample, or the like. According to various embodiments, at least one of the denser first material and the less-dense second material is insoluble in the other of the first material and the second material.

According to various embodiments, a microfluidic device is provided for marking a sample with a denser first material in the form of an identifiable marker, for example, with a marker that is insoluble in the sample and optically detectable. For example, the microfluidic device can be used for marking a biological sample with a nanoparticle, for example, with a nanobarcode. The first material can have a density that is greater than the density of remaining components of a sample, including at least one less-dense second material. The first material can be insoluble in water at 25° C. and/or can include multi-metallic colloidal rod particles. The microfluidic device can include a processing pathway that can include as a separation region a material-trapping region that can be used to trap a denser first material and separate it from a less-dense second material, for example, to separate the first material from a carrier used to deliver the first material into the microfluidic device. The material-trapping region can include first and second inlets and an outlet and can be disposed radially outwardly of the inlets and the outlet with respect to an axis of rotation around which the microfluidic device spins in operation. The material-trapping region can be disposed further away from an inlet to the processing pathway than is either the inlet or the outlet.

According to various embodiments, a method of separating a denser first material from a less-dense second material, in a microfluidic device, is provided. The method can include providing a microfluidic device that includes a processing pathway including a separation region, separating a denser first material from a less-dense second material in the separation region, and then removing the less-dense second material from the microfluidic device. The method can include subsequently mixing the separated denser first material with a sample or material to be treated. The method can include one or more of: reacting one or more sample components with one or more denser first material to form a mixture; separating marked components from other components of a sample; washing a separated component; re-suspending or re-mixing washed and/or marked components; and removing washed and/or marked components from the microfluidic device. The method can include introducing the denser first material into the microfluidic device, or the denser first material can be pre-loaded into the microfluidic device, for example, into the separation or material-trapping region. The separating can involve spinning the microfluidic device to generate centripetal forces.

BRIEF DESCRIPTION OF THE DRAWINGS

FIG. 3*a* is a top view of a valve that can be included in a microfluidic device according to various embodiments, wherein two recesses in a substrate are separated by an intermediate wall formed from a deformable relatively inelastic material when compared to the elasticity of a cover layer for the valve;

FIG. 3*b* is a cross-sectional side view of the assembly shown in FIG. 3*a*, taken along line 3*b*-3*b* of FIG. 3*a;*

FIG. 4*a* is a top view of the assembly shown in FIG. 3*a* along with a deformer device, and after initiation of an intermediate wall deforming step;

FIG. 4*b* is a cross-sectional side view of the assembly and deformer shown in FIG. 4*a*, taken along line 4*b*-4*b* of FIG. 4*a*, and showing the contact surface of the deformer advancing toward the intermediate wall;

FIG. 5*a* is a top view of the assembly shown in FIG. 3*a* but wherein the intermediate wall is in a deformed state following contact of the deformer with the intermediate wall;

FIG. 5*b* is as cross-sectional side view of the assembly shown in FIG. 5*a* taken along line 5*b*-5*b* of FIG. 5*a*, showing the contact surface of the deformer retracting from the intermediate wall, and wherein the intermediate wall is in a deformed state;

FIG. 6*a* is a partial cut-away top view of a fluid manipulation valve assembly that can be used in a microfluidic device according to various embodiments, and shown in an initial non-actuated stage;

FIG. 6*b* is a cross-sectional side view of the fluid manipulation valve assembly shown in FIG. 6*a*, taken along line 6*b*-6*b* of FIG. 6*a;*

Figure 1A:
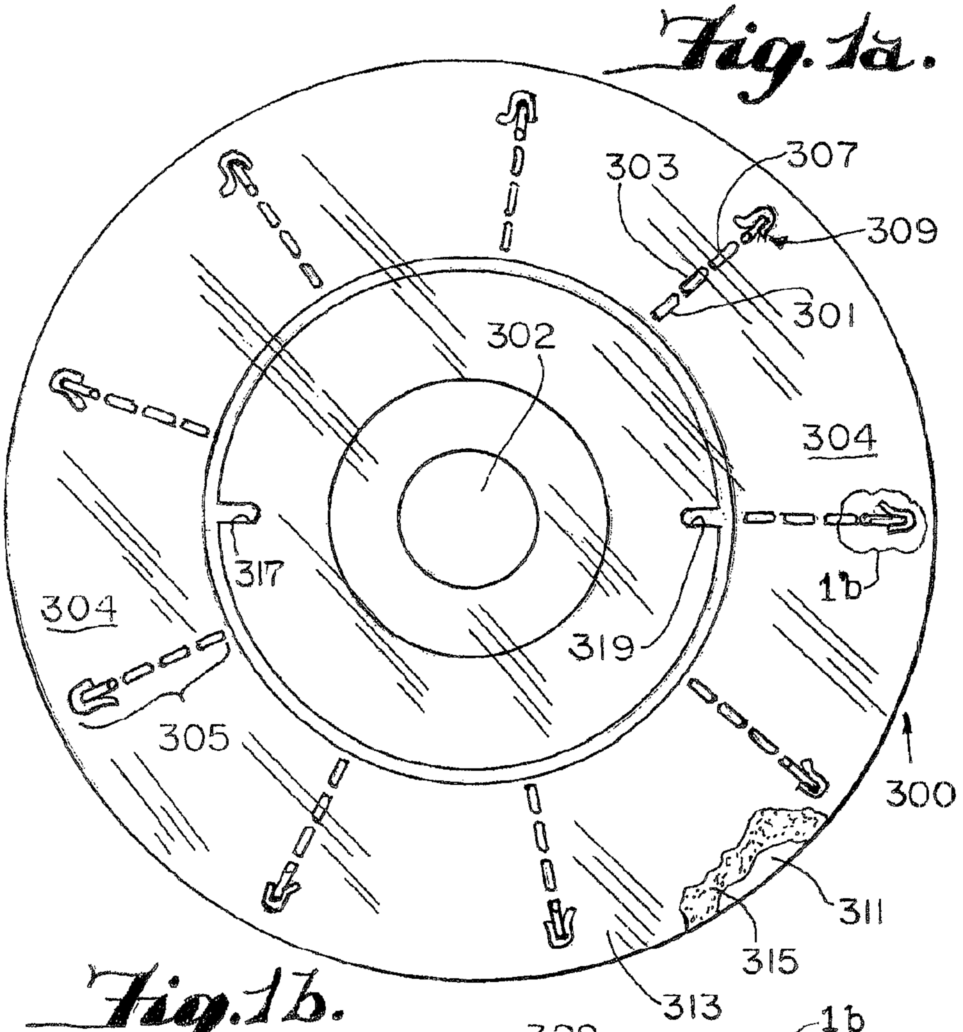
FIG. 1*a* is a top plan view of a microfluidic device according to various embodiments.

It is intended that the specification and examples be considered as exemplary only. The true scope and spirit of the present teachings include various embodiments.

DESCRIPTION OF VARIOUS EMBODIMENTS

According to various embodiments, a microfluidic device is provided that can be used to separate a denser first material from a less-dense second material, by using centripetal force. The less dense second material can then be removed from the microfluidic device while leaving the denser first material in the microfluidic device. Exemplary materials that can be separated using the microfluidic device can include an identifiable marker, a purification material, ion-exchange beads, ion-exchange resins, a grease, a resin, or other treatment particles or treatment materials. Such materials can be separated from remaining components of a sample, for example, from remaining components of a liquid sample, of an aqueous biological sample, or the like. According to various embodiments, at least one of the denser first material and the less-dense second material is insoluble in the other of the first material and the second material.

According to various embodiments, a microfluidic device can be provided for marking a sample, or a second material, with a denser first material, for example, with a first material that is optically detectable and insoluble in the sample or second material. For example, the microfluidic device can be used for marking a biological sample with a nanoparticle, for example, with a nanobarcode. The first material can have a density that is greater than the density of a sample or second material that is to be mixed with the first material. The denser first material can be insoluble in water at 25° C. The denser first material can include multi-metallic colloidal rod particles. The microfluidic device can include a separation chamber having a material-trapping region, for example, a marker-trapping region, that can be used to separate the denser first material from a second material. An exemplary separation can involve separating a denser first material from a carrier used to deliver the first material into the microfluidic device. The material-trapping region can be, for example, a purification resin-trapping region. The separation chamber can include two inlets and an outlet and can be disposed radially outwardly of both inlet and the outlet, with respect to an axis of rotation about which the microfluidic device spins in operation.

According to various embodiments, the microfluidic device can be of the size, shape, and general layout, of a compact disk (CD). According to various embodiments, the microfluidic device can be a card, for example, a rectangular microfluidic device card. The card can include one or more notch, cut-off corner, recess, pin, or other feature that can be used to orient the card in a card processing and/or analyzing device, for example, in a device holder of a rotating platen. The microfluidic device can be adapted to fit into a recessed microfluidic device holder on or in a rotating platen. The platen can be attached to or connected with a system that can include, for example, a drive unit, to spin the microfluidic device. The system can include a heater to heat the microfluidic device, an agitator to agitate the microfluidic device, a control unit to control a drive unit or heating unit, and/or other fluid manipulation means for otherwise manipulating or processing the microfluidic device and/or a sample disposed therein.

According to various embodiments, the microfluidic device can include a monolithic structure. The microfluidic device can include at least two regions adapted to retain solutions or other reagents. The regions can be, for example, chambers, channels, wells, reservoirs, recesses, conduits, or the like. The microfluidic device can include one or more valves that can be adapted to render at least two regions of the microfluidic device in fluid communication with each other, for example, to render a product chamber in fluid communication with the separation chamber. The microfluidic device can have a first side and a second side. Valves, regions, fluid passages, chambers, channels, reservoirs, or the like, or combinations thereof, can be located on or in the first side, on or in the second side, or on or in both sides of the microfluidic device. Valves or fluid passages can connect regions on or in the first side of the microfluidic device to regions on or in the second side of the microfluidic device.

According to various embodiments, the regions, valves, fluid passages, chambers, channels, reservoirs, or the like, can each have at least one sidewall. Each feature can be adapted to retain, contain, receive, restrain, archive, hold, and/or dispense a sample, reactant, reaction component, solution, carrier, vehicle, reagent, liquid, or other composition, or a combination thereof. The regions can be adapted to retain reactants during chemical reactions, for example, during a polymerase chain reaction, during a ligase chain reaction, during an oligonucleotide ligase assay, during an endonuclease assay, or during a nucleic acid amplification or sequencing reaction, or during a combination of such reactions. The regions can be adapted to perform filtration or purification of reagents, solutions, samples, or the like.

One or more cover layers can cover the first and/or second sides of the microfluidic device. The cover layer can be optically clear. The cover layer can be thermally conductive. The cover layer can be elastically deformable or semi-elastically deformable. The cover layer can be in the form of a sheet, a film, a substrate, a tape, or a combination thereof. Adjacent sections of the cover layer can be made of one or more different materials or of one material.

Examples of microfluidic device features and systems for spinning, heating, cooling, and otherwise processing microfluidic devices, that can be useful in or with the microfluidic devices described herein, are described, for example, in U.S. patent application Ser. Nos. 10/336,274, filed Jan. 3, 2003, 10/336,330, filed Jan. 3, 2003, 10/336,706, filed Jan. 3, 2003, 10/403,640, filed Mar. 31, 2003, 10/403,652, filed Mar. 31, 2003, 10/426,587, filed Apr. 30, 2003, 10/625,436, filed Jul. 23, 2003, 10/625,449, filed Jul. 23, 2003, 60/398,777, filed Jul. 26, 2002, 60/398,851, filed Jul. 26, 2002, 60/398,934, filed Jul. 26, 2002, 60/398,946, filed Jul. 26, 2002, and 60/399,548, filed Jul. 30, 2002, all of which are incorporated herein in their entireties by reference.

According to various embodiments, the higher density first material can be separable from, and/or insoluble in, a sample that the first material is to be mixed with. For example, the higher density first materials described herein can include nanoparticles. Exemplary nanoparticles and their uses are described in detail in U.S. patent application Ser. No. 09/598,395, filed Jun. 20, 2000, and U.S. patent application Ser. No. 09/969,518, filed Oct. 2, 2001, both of which are incorporated herein in their entireties by reference.

According to various embodiments, the rod-shaped nanoparticles can have a composition that is varied along the length of the rod. These particles are referred to as nanoparticles or nanobarcodes, though in reality some or all dimensions can be in the micron size range. These particles can be suspended in another substance, for example, suspended in a biochemical sample.

According to various embodiments, the first denser material can be nanoparticles. Free-standing nanoparticles can include a plurality of segments, wherein the particle length can be from about 10 nm to about 50 μm, and the particle width can be from about 5 nm to about 50 μm. The segments of the particles can include materials such as, for example, a metal, any metal chalcogenide, a metal oxide, a metal sulfide, a metal selenide, a metal telluride, a metal alloy, a metal nitride, a metal phosphide, a metal antimonide, a semi-conductor, a semi-metal, an organic compound or material, an inorganic compound or material, a particulate layer of material, a composite material, or a combination thereof. The segments of the particles can include a polymeric material, a crystalline material, a non-crystalline material, an amorphous material, a glass material, or a combination thereof.

According to various embodiments, the higher density first materials can be "functionalized", for example, by having their surface coated with a functional group, for example, with an IgG antibody. The functional group can be attached to selected segments, to all segments, to the body of the material, to one tip of the material, to both tips of the material, or to a combination thereof. The functionalization can actually coat segments of the material, for example, a nanoparticle, or can coat the entire material. The functional groups that can be used can include organic compounds, such as antibodies, antibody fragments, oligonucleotides, inorganic compounds, or combinations thereof. Such functional groups can include a detectable tag or can include a species that can bind to, or bind on, a detectable tag.

According to various embodiments, functionalized higher density first materials can be used in methods that include one or more of: reacting one or more sample components with one or more higher density first materials to form a reacted or marked component; separating a reacted or marked component from one or more remaining components of a sample; washing a separated, and reacted or marked, component; re-suspending or re-mixing a washed component that has been reacted or marked; and removing a washed, and reacted or marked, component from the microfluidic device. The method can include first introducing a functionalized higher density first material into a microfluidic device, or preloading into a microfluidic device a functionalized higher density first material. For example, according to various embodiments, a functionalized marker can be pre-loaded into a marker-trapping region of the device. The separating can involve spinning the microfluidic device to generate centripetal forces.

According to various embodiments, an assembly or collection of particles can include a plurality of different types of particles, wherein each particle can be from about 20 nm to about 50 μm in length and can include one or more segments. The types of particles can be differentiable from each other. The particle types can be differentiable based on differences in the length, width, or shape of the particles, or a combination thereof. Differentiation can be based on the number, composition, length, and/or pattern of the segments. The particles can be differentiable based on the nature of their functionalization, on physical properties, for example, as measured by mass spectrometry or light scattering, on chemical reactivity, on fluorescence, on electrical resistivity, and/or based on a combination of these properties.

According to various embodiments, the denser first material can include nanoparticles that can be manufactured by the electrochemical deposition of metals inside a template. The process can include electroplating in an ultrasonication bath and controlling the temperature of the deposition environment, such as by using a re-circulating temperature bath. A plurality of different types of nanoparticles can be manufactured simultaneously or in parallel. According to an exemplary method, a plurality of templates can be held in a common solution chamber. Electrochemical deposition can be accomplished by controlling deposition at each membrane by applying current selectively to predetermined electrodes associated with each membrane. An apparatus for the manufacture of suitable nanoparticles can include a plating solution cell, a defined-pore size template, a device for applying a current to cause electrochemical deposition of a metal into said template, a device for agitating the plating solution such as an ultrasonic transducer, temperature control means, or combinations thereof. An apparatus for the simultaneous manufacture of a plurality of different types of nanoparticles can include a solution chamber, a plurality of templates, a device for selectively applying a current to each of said templates, a control device for operating the apparatus, or combinations thereof.

According to various embodiments, segmented nanoparticles can be constructed using a porous template manufactured by standard photolithographic techniques and can include exposing a pattern on a resist-coated substrate or multi-layer stack and then etching the exposed pattern to form pores.

Nanoparticles can be formed by exposing a pattern on a resist-coated substrate including one or more layers of metal, then etching the exposed pattern to form free-standing nanoparticles. Nanoparticles can be manufactured by electrochemical deposition in an alumina or polycarbonate template, followed by template dissolution. Nanoparticles can be prepared by alternating electrochemical reductions of metal ions, or by other means, with or without using a template material.

According to various embodiments, the nanoparticles that can be used in devices and methods described herein can each have a length of up to about 1 millimeter (mm), or a length of from about 10 nanometers (nm) up to about 100 microns (μm), for example, from about 20 nm up to about 50 μm, or from about 1 μm to about 15 μm. The nanoparticles can each have widths of from three nanometers up to of about 10 microns, for example, widths of from about 30 nm to about 1,000 nm, or from about 50 nm up to about 500 nm. Each nanoparticle can have a depth, a diameter, or both. If the nanoparticles can each have a depth and/or a diameter the dimension or dimensions can be the same as mentioned about with respect to the width of each nanoparticle, and the depth and/or diameter can be the same as, or different than, the width.

According to various embodiments, the nanoparticle can include two or more different materials that alternate with one another along the length of the particle, and a plurality of different materials can be used, for example, 5 different materials or 25 different materials. Likewise, the segments can include non-metallic material, including but not limited to polymers, oxides, sulfides, semiconductors, insulators, plastics, monolayer thin films of organic or inorganic species.

According to various embodiments, when the nanoparticles are made by electrochemical deposition, the length of the segments, as well as their density and porosity, can be adjusted by controlling the amount of current, or electrochemical potential, passed in each electroplating step. As a result, the nanoparticles can be made to resemble a "bar code" but on a nanometer-sized scale, with each segment length and identity being programmable in advance.

Other forms of deposition can also yield the same or similar results. Deposition can be accomplished via electroless processes and in electrochemical deposition processes by controlling, for example: the area of the electrode; the heterogeneous rate constant; the concentration of the plating material; the electrical potential; and combinations thereof. These parameters are collectively referred to herein as electrochemical deposition parameters. The same or similar results can be achieved using another method of manufacture in which the length or other attribute of the segments can be controlled. The diameter of the particles and the segment lengths can be controlled to be of nanometer-sized dimensions. The overall length of the nanoparticle can be controlled to be able to be visualized directly with an optical microscope, and a detection method can exploit differential reflectivities of different metal components to determine the nanoparticle type or code.

According to various embodiments, the denser material can be a particle, for example, a marker, defined in part by size and/or by the existence of at least two segments. A segment can represent a region of the particle that can be distinguishable, by any one of a variety of means, from one or more adjacent regions of the particle, for example, based on different reflectivities. Segments of the particle can bisect the length of the particle to form regions that have about the same cross-section and width as the whole particle, while representing a portion of the length of the whole particle. A segment can be composed of the same materials as, or a different material from, one or more adjacent segments. However, not every segment of the barcode needs to be distinguishable from all other segments of the particle. For example, a particle can be composed of two types of segments, for example, gold (Au) and platinum (Pt), and contain from about 10 to about 20 different segments, for example, alternating segments of gold and platinum. Another exemplary particle has the segment sequence Pt—Pt—Pt—Au—Pt—Au—Au—Pt.

According to various embodiments, the denser material can include a particle that can contain at least two segments, for example, at least about four segments or at least about 100 segments. The particles can have, from about two segments to about 30 segments or from about three segments to about 20 segments. According to various embodiments, the particles can have any number of different types of segments, the particles can have from about two to about 10 different types of segments, for example, from about two to about five different types of segments.

A segment of a multi-segment particle is defined herein as a discrete portion of the particle which is distinguishable from one or more adjacent segments of the same particle. The ability to distinguish between segments can include distinguishing by any physical or chemical analysis including but not limited to electromagnetic analysis, magnetic analysis, optical analysis, reflectivity analysis, spectrometric analysis, spectroscopic analysis, and mechanical analysis.

Adjacent segments of a multi-segment particle can include or be composed of the same material, and can be distinguishable from one another by any of the analysis techniques mentioned above. For example, different phases of the same elemental material, enantiomers of an organic polymeric material, different surface morphologies, and combinations thereof, can be used to provide distinguishable adjacent segments. In addition, a rod constructed of a single material can be distinguished from others, for example, by functionalization on the surface, or by including segments of different diameters. Particles that include organic polymeric materials can have segments distinguishable from one another on the basis of different dyes incorporated therein that provide the respective segment with a different relative optical property compared to at least one other type of segment.

According to various embodiments, the first material can be a nanoparticle and can include segments with different respective compositions. For example, a single particle can include one segment that includes a metal and one segment that includes an organic polymeric material.

The segments can be made of any suitable material. The segments can include, for example, silver, gold, copper, nickel, palladium, platinum, cobalt, rhodium, iridium, a metal chalcognide, a metal oxide, for example, cupric oxide or titanium dioxide, a metal sulfide, a metal selenide, a metal telluride, a metal alloy, a metal nitride, a metal phosphide, a metal antimonide, a semiconductor, a semi-metal, or a combination or alloy thereof. A respective segment can include an organic monolayer, an organic bilayer, a molecular film, monolayers of organic molecules, or self-assembled controlled layers of molecules. The segments can be associated with a variety of metal surfaces.

A respective segment can include any organic compound or material, inorganic compound or material, or organic polymeric material, including the large body of mono and copolymers known to those skilled in the art. Biological polymers, such as peptides, oligonucleotides and polysaccharides can be components of a segment. Segments can include particulate or granulate materials, for example, metals, metal oxide, or organic granulate materials. Segments can be composite materials, for example, a metal-filled polyacrylamide, a dyed polymeric material, or a porous metal. The segments of the particles can include polymeric materials, crystalline or non-crystalline materials, amorphous materials, or glasses.

According to various embodiments, the segments can be distinguished by notches on the surface of the particle, or by the presence of dents, divits, holes, vesicles, bubbles, pores, or tunnels that are formed on in the surface of the particle. Segments can also be distinguished by a discernable change in the angle, shape, or density of such physical attributes, or in the contour of the surface. According to various embodiments, the nanobarcode particle can be coated, for example, with a polymer, or with glass. The segment can include or consist of a void between other materials.

The length of each segment can be from about three nm to about 50 μm, for example, from about 50 nm to about 20 μm. The interface between segments need not be perpendicular to the length of the particle, and need not be a smooth line of transition. The composition of one segment can be blended into the composition of the adjacent segment. For example, between segments of gold and platinum, there can be a 5 nm to 5 μm region that can include both gold and platinum, for example, alloyed together. For any given particle, the segments can be of any length relative to the length of one or more other segments of the particle.

As described above, the particles can have any cross-sectional shape. According to various embodiments, the particles can be generally straight along the lengthwise axis. According to various embodiments, the particles can be curved or helical. The ends of the particles can be flat, convex, or concave. The ends can be spiked or pencil-tipped. Sharp-tipped embodiments of the particles can be used in, for example, Raman spectroscopy applications, or in other applications where energy field effects can be important in analysis. The ends of any given particle can be the same or different. The contour of the particle can be advantageously selected to contribute to the sensitivity or specificity of the assays. For example, an undulating contour can enhance "quenching" of fluorophores located in the troughs.

According to various embodiments, an assembly or collection of dense materials, for example, nanoparticles, can be prepared and/or used. The members of the collection can be identical or the collection can include a plurality of different types of materials and/or different types of particles. In collections of identical particles, the length of substantially all of the particles that are within a size range of from about one μm to about 15 μm can vary up to about 50%. Segments of about 10 nm in length can vary in length by about +/−0.5 nm while segments that are about one μm in length can vary in length by up to about 50%. The widths of the particles can vary from one another by about 10% to about 100%, for example, less than about 50% or less than about 10%.

Assemblies or collections of dense materials, for example, a collection of different nanoparticles, can include a plurality of particles that are identifiably differentiable from one another. "Assembly" or "collection," as used herein, does not necessarily mean that the materials that make up such an assembly or collection are ordered or organized in any particular manner. A collection can be made up of a plurality of different types of materials or particles or can be made up of a plurality of the same type of materials or particles. According to various embodiments, each material of the collection can be functionalized in the same manner or in a respective different manner. The functionalization can be different and specific for each specific type of material. The collection can include from about two to about $10^{12}$ different and identifiable particles. Assemblies can include more than 10, more than 100, more than 1,000, or more than 10,000 different types of particles, for example, different types of optically-identifiable marker particles. The materials or particles in a collection can be segmented. The collection can be of particles and can, but does not necessarily have to, contain particles each including a plurality of segments.

The denser material can include particles having mono-molecular layers. Mono-molecular layers can be found at the tips or ends of the particles, or between segments. Examples of mono-molecular layers between segments are described in the section entitled ELECTRONIC DEVICES set forth in U.S. patent application Ser. No. 09/598,395, filed Jun. 20, 2000, which is incorporated herein in its entirety by reference. The denser material can be mixed with or combined with a fluid, for example, a liquid. The denser material can be mixed with water or an aqueous solution. The denser material can be dispersed in a fluid to form a suspension, a mixture, an emulsion, or a combination thereof.

According to various embodiments, the denser first material can include size-exclusion ion-exchange materials, for example, beads, or coated structures, as described in U.S. patent application Ser. No. 10/414,179 filed Apr. 14, 2003, which is incorporated herein by reference in its entirety. According to various embodiments, the less-dense second material can include a biological sample, for example, an aqueous sample including one or more nucleic acid sequences, sought to be treated by the size-exclusion ion-exchange material. According to various methods, the denser first material and the less-dense second material are contacted with each other for a period of time greater than about 15 seconds, prior to a separation operation as described herein. For example, the contact time can be greater than about one minute, greater than about two minutes, or greater than about five minutes.

With reference to the drawings, FIG. 1*a* is a top plan view of a microfluidic device 300 according to various embodiments. Region 304 of the microfluidic device 300 includes a plurality of fluid-processing pathways 305 that are generally radially arranged and can be parallel or non-parallel to a radius of the microfluidic device 300. Each fluid-processing pathway can include a plurality of features, for example, a loading chamber 301, a reaction chamber 303, a purification chamber 307, and a separation chamber 309, as shown. The separation chamber 309, can be, for example, a marking chamber. An enlarged view of section 1*b* of the microfluidic device, including separation chamber 309, is shown in FIG. 1*b*.

The various features of each pathway 305 can be made to be in fluid communication with at least one adjacent feature through a valve or other interruptible or openable passageway. Closing valves can be included to interrupt fluid communication between two or more of the features. More details of opening and closing valves are set forth below, for example, in connection with the descriptions of FIGS. 3*a*-11*b*.

The microfluidic device 300 can include a substrate 311, a cover or cover layer 313, and an adhesive layer 315 that adheres the cover 313 to the substrate 311. The adhesive layer 315 can be used as a valve closing material, as discussed below, for example, in connection with the description of FIGS. 7*b*, 10*b*, and 11*b*.

Figure 1B:
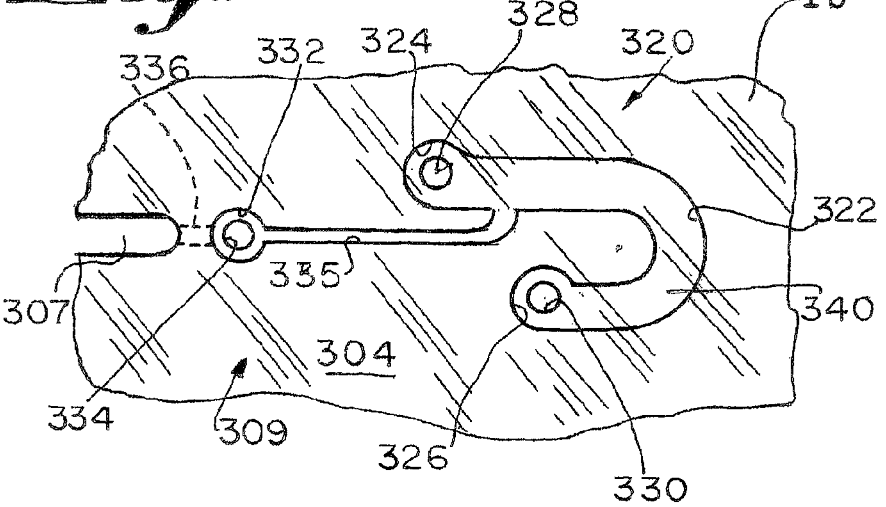
FIG. 1*b* is an enlarged view of region 1*b* of the microfluidic device shown in FIG. 1*a;*

The microfluidic device 300 shown in FIGS. 1*a* and 1*b* can include alignment recesses or holes 317, 319 for aligning the microfluidic device 300 on or in a spinnable platform, on or in a rotating drive unit, or on or with an alignment pin or drive pin of such a device. Microfluidic device 300 can be rotated about an axis of rotation 302, for example, when disposed on a rotating platen (not shown). A respective fluid sample can be moved through a respective pathway 305, for example, through open valves and by application of centripetal force.

FIG. 1*b* is an enlarged view of region 1*b* of the microfluidic device 300, shown in FIG. 1*a*. As can be seen in FIG. 1*b*, the separation chamber 309 can include a material containment region 320 that has a generally U-shape and includes a first end 324, a second end 326, and a material separation region or mid-section 340. The first end 324 of the material containment region 320 can be closer to the axis of rotation 302 (shown in FIG. 1*a*) than is the second end 326. One or more denser first materials (not shown), for example, one or more nanoparticles, can be inserted into an input opening 328 along with a less-dense second material, for example, a delivery vehicle or carrier (not shown). The first material and second material can be moved into and centrifugally separated in the material containment region 320. The dense first material can be moved into the material separation region 340 by using centripetal force. For example, the microfluidic device 300 can be spun around axis 302 at a speed of from about 60 revolutions per minute (RPM) to about 10,000 RPM or from about 100 RPM to about 1,000 RPM to generate a centripetal force.

The separation chamber 309 can include a first input opening 334 that can be made to be in fluid communication with an adjacent chamber 307 of the pathway 305 (FIG. 1*a*). Alternatively, or additionally, a sample or a reaction component can be introduced into separation chamber 309 directly through first input opening 334. The first input opening 334 can be provided with a frangible seal. The input opening 328 is also referred to herein as a second input opening. The separation chamber 309 can be provided with an output opening 330. Any or all of first input opening 334, second input opening 328, and output opening 330, can be provided with a seal, for example, a frangible hermetic sealing layer.

According to various embodiments, pressure created by the movement of the second material and the first material can be vented to the atmosphere through vent 334, and negative pressure within the separation chamber 309 can be relieved through vent 334. The denser first material can be separated from its carrier by using, for example, centripetal force. For example, microfluidic device 300 can be spun around axis 302 at from about 1,500 RPM to about 8,000 RPM, or from about 2,500 RPM to about 5,000 RPM, during which spinning the denser first material can be separated from a less-dense second material and deposited against sidewall 322. The second material, separated from the denser first material, can then be removed from the material containment region 320 through output opening 330; without removing the denser first material deposited on the sidewall 322.

The separation chamber 309 can have a length of, for example, from about 100 μm to about 2.0 cm, or from about 1.0 mm to about 1.5 cm. The separation chamber 309 can have a depth of, for example, from about 2.0 μm to about 5.0 mm, or from about 100 μm to about 1.5 mm. The separation chamber 309 can have a depth of, for example, from about 2.0 μm to about 5.0 mm, or from about 100 μm to about 1.5 mm.

A sample (not shown) can be moved into sample retainment region 338 using, for example, centripetal force, by spinning microfluidic device 300 around axis 302. Sample, for example, from a purification chamber 307, can be loaded into separation chamber 309 by forming a fluid communication between the purification chamber 307 and the separation chamber 309, for example, by opening a valve. An exemplary valve is a Zbig valve 336 (described below) located between the sample purification chamber 307 and the first input opening 334. In an exemplary method, the sample can be moved from purification chamber 307 into separation chamber 309 by spinning microfluidic device 300 around axis 302 at a speed of from about 100 RPM to about 1,000 RPM. The sample can thus be moved through a loading channel 335 and into material containment region 320 where the sample can then mix with the pre-deposited first material that had been previously trapped in the material separation region 340. For example, the sample can be mixed with an optically detectable denser first material that had been deposited along sidewall 322 of material containment region 320. By way of example, the denser first material can be a treatment material, a purification material, an ion-exchange material, an identifiable marker, or a combination thereof. Other denser first materials can also be used and include chemically detectable markers, electrically detectable markers, and the like, as are recognizable to those of skill in the art.

Mixing of a sample and a separated denser first material can occur in the microfluidic device by using, for example, vibration, shaking, pulsation, agitating, sonication, ultrasonication, or the like. For example, the material containment region 320 can be agitated using an ultrasonic finger (not shown), wherein the ultrasonic finger can be a device that agitates the material containment region 320 at a single point or at several points that are in close proximity to one another. The mixing of the sample and the optically detectable first materials can occur at a liquid—air interface. Air bubbles or gas bubbles can be provided in or generated in the separation chamber 309.

According to various embodiments, the denser material is an optically detectable marker material. By mixing the optically detectable marker material with a sample, the optically detectable marker material can label or mark the sample. For example, depending upon the type of marker material used, the marker material can biochemically react with and bind to one or more components of the sample. The bound sample can then be optically detected and/or be separated from the remaining, unbound sample by, for example, depositing the bound sample onto sidewall 322 using centripetal force. The remaining, unbound sample can then be removed from the material containment region 320 by moving the remaining, unbound sample from the material containment region 320, through outlet 330, and to a waste or other receptacle via a liquid handling device, for example, as shown and described below in connection with FIGS. 2*a*-2*e*. The unbound sample can be removed from the material containment region by creating a pressure gradient, such as by suction, a vacuum or partial vacuum, or with positive pressure, or by displacement or flushing-out with a carrier, such as water. The bound sample can be removed from the material containment region 320 by introducing a carrier into the material containment region 320 through inlet 328, then mixing the bound sample with a carrier or vehicle, for example, by ultrasonication. The carrier and bound sample can then be removed from the material containment region 320 by creating a pressure gradient, such as by suction, a vacuum or partial vacuum, or with positive pressure, or by displacement with a second aliquot of carrier, such as water. The valve 336 and/or the first input opening 334 can be closed prior to removing marked, unmarked, unbound and/or bound sample from the material containment region 320.

Figure 2A:
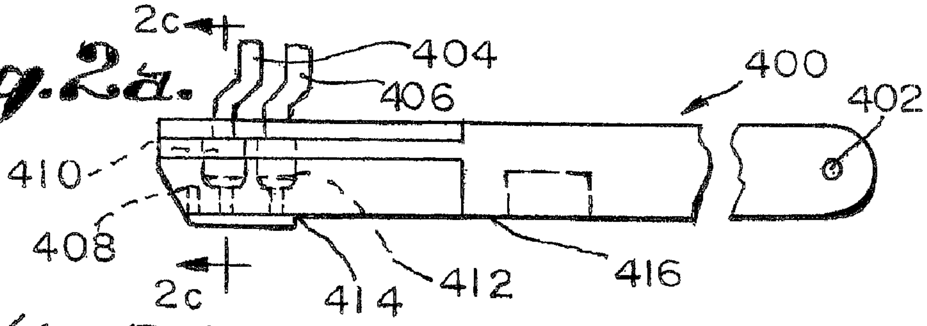
FIG. 2*a* is a side view in partial phantom of a fluid manipulating arm according to various embodiments.

FIG. 2*a* is a side view of fluid handling arm 400 that can be used to manipulate fluids in microfluidic device 300. The handling arm 400 can contact microfluidic device 300, for example, at inlet 334 and outlet 330. The fluid handling arm 400 can move in a generally vertical direction by rotating about an axis of rotation 402. Fluid handling arm 400 can contain fluid handling heads, pipes, tubes, passages, or the like. An inlet hose 404 can be connected to or incorporated in the fluid handling arm 400 and can direct a carrier or flushing liquid, such as water, or a carrier or flushing gas, such as air, into the material containment region 320, for example, through the second input opening 328. The carrier or flushing fluid or gas can pass from inlet hose 404 through a cavity 410 and through a gasket 414 that is adapted to create a seal between the microfluidic device 300 and the fluid handling arm 400.

According to various embodiments, the fluid handling arm 400 can include one or more internal cavities, for example, cavity 410. Cavity 410 can house an injector, for example, attached to the end of inlet hose 404. An outlet hose 406 can be connected to or incorporated in the fluid handling arm 400 and can direct a carrier liquid, such as water, or a carrier gas, such as air, along with marked, unmarked, unbound, and/or bound sample from the marker containment region 320 through output opening 330. The fluid, gas, and sample, or a combination thereof, can pass from output opening 330, through gasket 414, through cavity 412, and into outlet hose 406. The cavity 412 can house an injector, for example, attached to the end of outlet hose 406. Cavity 408 can house an opening device (not shown), a closing device (not shown), or both, to open and/or close valves that are part of the microfluidic device, such as, for example, Zbig valve 336.

Figure 2B:
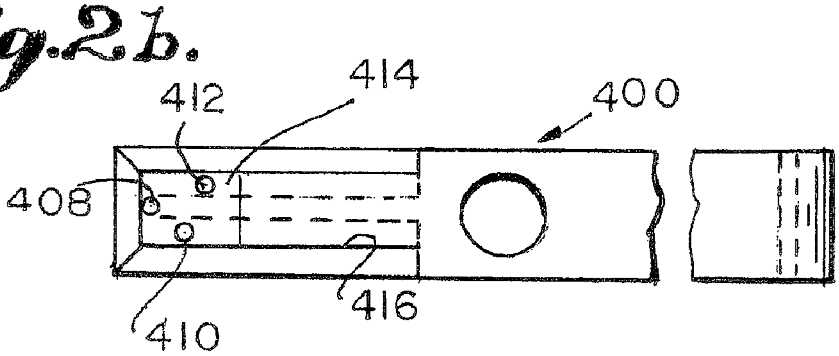
FIG. 2*b* is a bottom view of the fluid manipulating arm shown in FIG. 2*a;*

FIG. 2*b* is a bottom view of fluid handling arm 400. Gasket 414 is adapted to form a seal between the bottom surface 416 of fluid handling arm 400 and the microfluidic device 300. A gasket can be provided that is recessed in the fluid handling arm 400 and flush with the bottom surface 416. A gasket can be provided that is an integral part of the bottom surface of the fluid handling arm. According to various embodiments, the fluid handling arm 400 can be designed without a gasket but of a shape and/or material that forms a seal between bottom surface 416 and a surface of a microfluidic device.

Figure 2C:
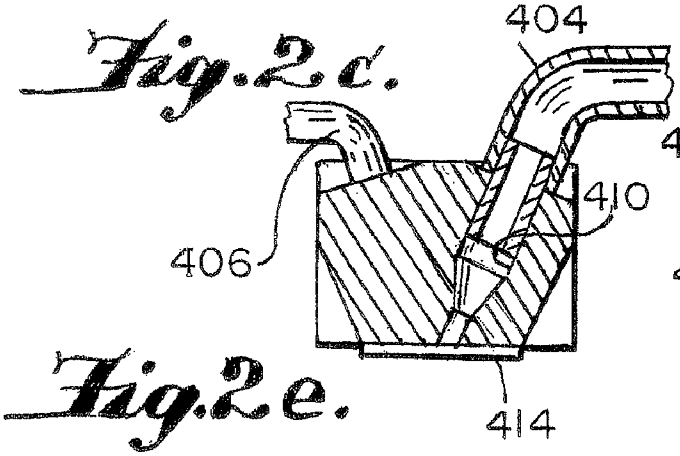
FIG. 2*c* is a cross-sectional end view taken along line 2*c*-2*c* of the fluid manipulating arm shown in FIG. 2*a;*

FIG. 2*c* is a cross-sectional view taken along line 2*c*-2*c* of FIG. 2*a*. Cavities 410 (shown) and 412 (FIG. 2*a*) can be made to be in fluid communication with, for example, an input opening and an output opening as discussed above. According to an exemplary embodiment, cavities 410 and 412 can be adapted to house injectors (not shown) that can mate with inlet 328 and outlet 330 of microfluidic device 300 (FIGS. 1*a* and 1*b*), and transfer gases or liquids into or out of microfluidic device 300. Cavity 410, for example, can be used as a material supply cavity and can provide a material supply opening that can communicate with inlet 328 of the microfluidic device. Cavity 412, for example, can be used as a material evacuating cavity and can provide a material evacuating opening that can communicate with outlet 330 of the microfluidic device. In FIG. 2*c*, a hose coupler 415 is shown in cross-section, inserted into and extending from cavity 410.

Figure 2D:
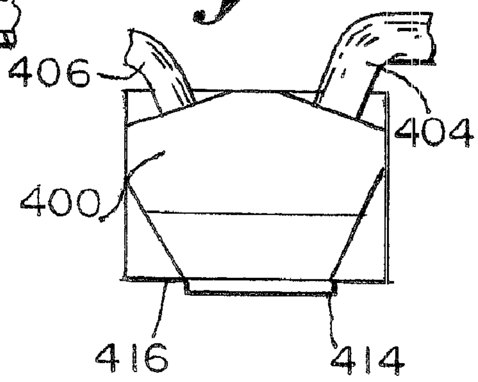
FIG. 2*d* is an end view of the fluid manipulating arm shown in FIG. 2*a;*

FIG. 2*d* is an end view of the liquid handling arm 400 shown in FIGS. 2*a*-2*c*, and shows gasket 414 on the bottom surface 416 of the handling arm 400.

Figure 2E:
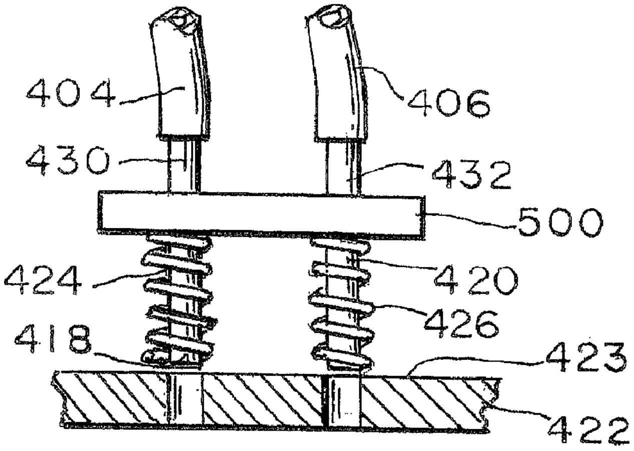
FIG. 2*e* is a schematic view of a portion of a fluid manipulating arm according to various embodiments.

FIG. 2*e* is a side view of a different type of fluid handling device that includes a fluid handling arm 500 and injectors 418 and 420 that are adapted to form a fluid-tight and gas-tight seal with a portion 422 of a microfluidic device, such as an elastic cover layer of a microfluidic device. Springs 424 and 426 can dampen and/or modulate the downward force of the fluid handling arm 500 against the portion 422 of the microfluidic device, and can assist in maintaining a fluid-tight and air-tight seal between the injectors 418 and 420 and the portion 422. Inlet hose 404 can be connected at a first end to an adapter 430 on the fluid handling arm 500, and can be connected at a second end to a fluid source, a gas source, a pressure generating device, or the like, or a combination thereof. Outlet hose 406 can be connected at a first end to an adapter 432 on fluid handling arm 500, and can be connected at a second end to a sample collection device, a waste receptacle, a vacuum source, or the like, or a combination thereof.

The injectors can be made from, for example, stainless steel, composite materials, aluminum, metal alloys, plastic materials, polymeric materials, or the like, or a combination thereof. The injectors can have any suitable inner diameter, for example, an inner diameter of from about 0.001 inch to about 0.01 inch, for example, of from about 0.005 inch to about 0.05 inch. The height of the fluid handling arm 500 can be from about 0.25 inch to about 0.75 inch. The length of the fluid handling arm 500 can be from about two inches to about ten inches. Springs, gaskets, or both, can be used to effect a fluid-tight and/or air-tight seal between the injectors and the contact portion or portions of the microfluidic device, for example, at the top surface 423 of portion 422.

According to various embodiments, the method can include reacting one or more sample components with one or more dense first materials in the separation chamber 309 to form a product, and then separating the product from remaining, less dense, components of the sample, for example, by applying centripetal force. According to various embodiments, an exemplary method involves marking a component of a sample with an identifiable marker. The sample can contain other remaining sample components that are not marked with the identifiable marker and that can be separated from the marked sample component. The remaining sample components can then be evacuated from the separation chamber 309 leaving only the marked sample component in the separation chamber 309. The separated product can then be re-suspended or re-mixed with a washing fluid, for example, water, and then separated again or removed with the fluid, for example, for further processing. A fluid handling arm as shown in FIGS. 2*a*-2*d*, or as shown in FIG. 2*e*, can be used to evacuate the remaining sample components from the separation chamber 309, to fill the separation chamber 309 with a washing fluid, and to remove a marked sample from separation chamber 309.

According to various embodiments, a system can be provided that can include a microfluidic device as described herein and one or more processing components, for example, a heater, a rotatable platen, a fluid handling arm, an ultrasonic device, an excitation source, a detector, or a combination thereof. The system can include, for example, a microfluidic device, a rotatable platen, a holder for holding the microfluidic device on or in the rotatable platen, and a drive unit operatively connected to rotate the rotatable platen. The system can include, for example, a microfluidic device, a holder for holding the microfluidic device, and an ultrasonic device capable of producing ultrasonic energy. The ultrasonic device can be operatively arranged relative to the holder to direct ultrasonic energy toward the material separation region of the microfluidic device when the microfluidic device is operatively held by the holder. The system can include, for example, a microfluidic device, a holder for the microfluidic device, and an electromagnetic excitation beam source operatively arranged relative to the holder to direct excitation beams toward the material separation region. The system can also include, for example, an electromagnetic emission beam detector operatively arranged relative to the holder to detect emission beams emitted from the material separation region. The system can include, for example, a microfluidic device and a fluid handling arm wherein the fluid handling arm includes a material supply opening and a material evacuation opening. The material supply opening and the material evacuation opening can be capable of simultaneously being aligned with at least one of the first and second input openings and with the output opening, respectively, of the microfluidic device. The fluid handling arm can include an alignment recess to operatively align the fluid handling arm with respect to the microfluidic device.

With reference to FIGS. 3*a*-11*b*, according to various embodiments microfluidic devices including a valved input opening leading to the separation chamber, the same as or similar to valve 336 shown in FIG. 1*b*, can include a pressure-sensitive one-way valve, a single use valve, a two-way valve, or the like. The valve can include an inelastically deformable barrier. For example, the valve can include a deformable barrier wherein one or more sidewalls of the valve can be deformed to close the valve. Alternatively, or additionally, the valve can include a barrier that can be deformed to open the valve. The valve can be or can include a Zbig valve as described in U.S. patent application Ser. No. 10/336,274, which is incorporated herein in its entirety by reference. The valve can include an elastic material cover layer. The valve can be any of the valves described, for example, in U.S. patent application Ser. Nos. 10/336,274 filed Jan. 3, 2003, 10/336,330 filed Jan. 3, 2003, 10/336,706 filed Jan. 3, 2003, 10/403,640 filed Mar. 31, 2003, 10/403,652 filed Mar. 31, 2003, 10/426,587 filed Apr. 30, 2003, 10/625,449 filed Jul. 23, 2003, 60/398,777 filed Jul. 26, 2002, 60/398,851 filed Jul. 26, 2002, 60/398,946 filed Jul. 26, 2002, and 60/399,548 filed Jul. 30, 2002, all of which are incorporated herein in their entireties by reference.

According to various embodiments, a microfluidic device including a separation chamber can also include one or more of the below-described openable, closeable, reopenable, and/or recloseable valves for the purpose of providing a fluid communication between, or for interrupting a fluid communication between the separation chamber and an adjacent sample-retainment feature, for example, an adjacent chamber or an adjacent channel or reservoir. The adjacent chamber can be located upstream or downstream, relative to the separation chamber, along a fluid processing pathway.

FIG. 3*a* is a top view of a microfluidic assembly 198 including a valve that can be used according to various embodiments. As shown in FIG. 3*a*, two chambers are initially kept separate, in the form of recesses 106 and 107, and are formed in a substrate layer 100. The recesses 106 and 107 are separated by an intermediate wall 108 that includes or is formed of a deformable material. The chambers can be, for example, a sample loading chamber and a separation chamber, respectively. The material of the intermediate wall can be inelastically deformable or elastically deformable. The valve also includes an elastically deformable cover layer 104.

If the material of the intermediate wall is elastically deformable, it can be less elastically deformable (have less elasticity) than the material of the cover layer, or at least rebound more slowly when compared to the material of the cover layer. As such, the cover layer can be capable of recovering or rebounding from deformation, more quickly than the intermediate wall material. Thus, if both the cover layer and the intermediate wall are elastically deformable but to different degrees, the cover layer can rebound from deformation more quickly than the intermediate wall material and a gap can therefore be provided therebetween, just after deformation. The gap can function as an opening that forms a fluid communication between the two recesses. For the sake of example, but not to be limiting, the intermediate wall material is described below as being inelastically deformable.

FIG. 3*b* is a cross-sectional side view of the assembly 198 shown in FIG. 3*a*, taken along line 3*b*-3*b* of FIG. 3*a*. As can be seen, the assembly 198 includes an elastically deformable cover layer 104 and a pressure-sensitive adhesive layer 102 disposed between the substrate 100 and the elastically deformable cover layer 104. The recess 106 is at least partially defined by sidewalls 116 and 118 and bottom wall 114 as shown in FIG. 3*b*. In the non-deformed state, intermediate wall 118 includes a top surface that is in contact with and sealed by the pressure sensitive adhesive 102 at interface 103.

FIG. 4*a* is a top view of the assembly 198 shown in FIG. 3*a* in deforming contact with a deformer 110 positioned after initiation of and during an intermediate wall-deforming step. FIG. 4*b* is a cross-sectional side view of the assembly 198 and deformer 110 shown in FIG. 4*a*, taken along line 4*b*-4*b* of FIG. 4*a*, and showing the contact surface 147 of the deformer 110 advancing toward and deforming the intermediate wall 108.

FIG. 5*a* is a top view of the assembly shown in FIG. 3*a* but wherein the intermediate wall is in a deformed state following contact of the deformer with and separation from the intermediate wall, that is, contact with the elastically deformable cover layer 104 and the adhesive layer 102 in between, the deformer and the intermediate wall.

FIG. 5*b* is a cross-sectional side view of the assembly 198 shown in FIG. 5*a* taken along line 5*b*-5*b* of FIG. 5*a*. FIG. 5*b* shows the contact surface of the deformer 110 retracting from the intermediate wall 108 leaving a portion 112 in a deformed state.

As can be seen in FIG. 4*b*, the deformer 110 deforms the cover layer 104, the pressure sensitive adhesive layer 102, and the intermediate wall 108. The intermediate wall 108 gives way to the deforming force of the deformer and begins to bulge as shown at 111. After the deformer 110 is withdrawn from contact from the assembly 198, the elastically deformable cover layer 104 and pressure sensitive adhesive layer 102 rebound to return to their original orientation, however, the inelastically deformable material of the intermediate wall 108 remains deformed after withdrawal of the deforming force such that intermediate wall 108 is provided with a depressed, deformed portion 112. The portion of the elastically deformable cover layer 104, including the pressure sensitive adhesive layer 102, adjacent the deformed portion 112 of the intermediate wall 108, is not in contact with the deformed portion 112 such that a through-passage 109 is formed allowing fluid communication between recesses 106 and 107.

FIG. 6*a* shows a partial cut-away top view of a substrate layer portion 222 of a fluid manipulation valve assembly 220 according to various embodiments. At least two recesses 228, 230 can be formed in the substrate layer 222, and can be separated by an intermediate wall 232. The intermediate wall 232 can define an area of a valve 226 that can be manipulated to control fluid communication between the two recesses 228, 230, for example, between a sample loading chamber and a marking chamber. The intermediate wall 232 can be formed from a deformable material that can be inelastically or elastically deformable. According to various embodiments, the entire substrate layer 222 can include an inelastically or elastically deformable material.

FIG. 6*b* is a cross-sectional side view of the valve 226 shown in FIG. 6*a*, taken along line 6*b*-6*b* of FIG. 6*a*. The valve 226 can include an elastically deformable cover including a cover layer 242 and an adhesive layer 244. The adhesive layer 244 can include, for example, a pressure sensitive or hot melt adhesive, disposed between the substrate layer 222 and the elastically deformable cover layer 242.

As shown in FIG. 6*b*, a height of the intermediate wall 232 between the recesses 228, 230 can be formed with a depression relative to a surface 224 of the substrate layer 222, thereby forming a recessed channel 234. Moreover, the non-depressed portion of the intermediate wall 232 can be flush with a top surface 224 of the recess-containing substrate layer 222 of the assembly 220. As illustrated in FIG. 6*b*, in the non-deformed state of the cover layer 242, the recessed channel 234 of the intermediate wall 232 can form a fluid communication 236 between the first recess 228 and the second recess 230. Therefore, in the non-deformed state of the elastically deformable cover, the valve 226 is in a normally open condition. According to various embodiments, the valve 226 of the fluid manipulation valve assembly 220 can be manipulated using mechanical pressure, and temperature, for example.

Figure 7A:
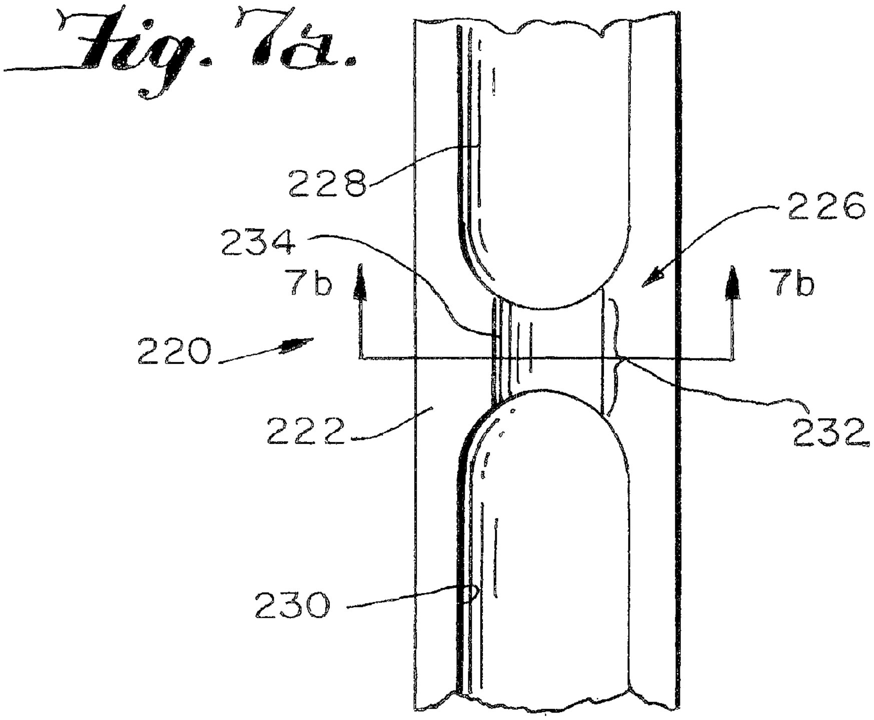
FIG. 7*a* is a top view of a fluid manipulation valve assembly that can be used according to various embodiments, and shown in a first stage of actuation.
Figure 7B:
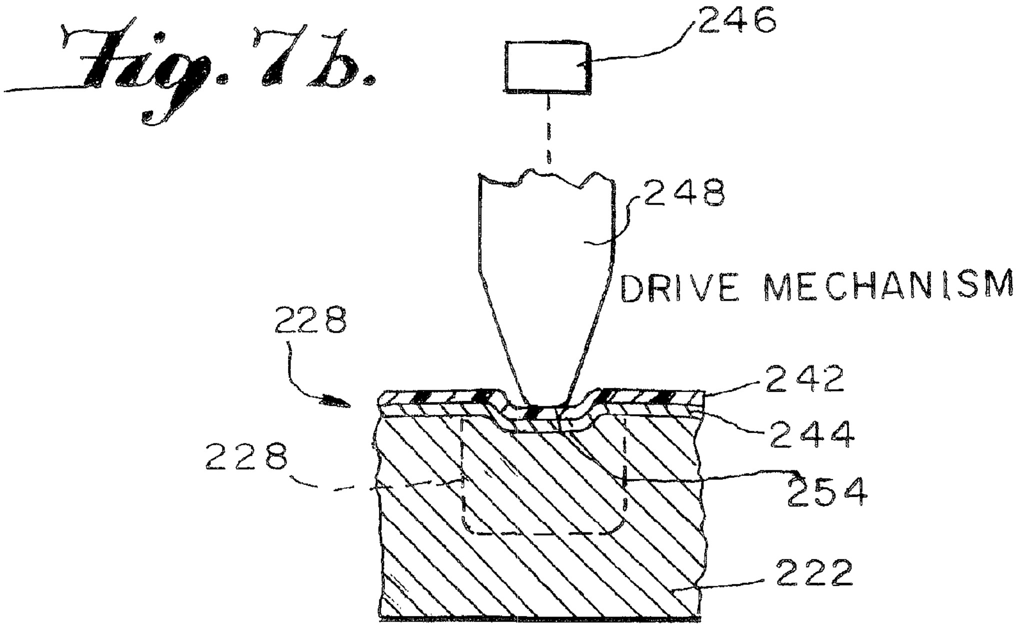
FIG. 7*b* is a cross-sectional side view of the fluid manipulation valve assembly shown in FIG. 7*a*, taken along line 7*b*-7*b* of FIG. 7*a*, and corresponding to the first stage of actuation.

FIGS. 7*a* and 7*b* show a top view and a cross-sectional side view, respectively, of the valve 226 of the fluid manipulation valve assembly 220 in the first valve closing condition. In FIG. 7*b*, the valve 226 is shown in deforming contact with a first deformer 248 positioned after initiation of, and during, the first valve closing condition. As can be seen in FIG. 7*b*, a drive mechanism 246 can be arranged to displace the first deformer 248 in a direction towards the cover layer 242 such that a contact surface 254 of the first deformer 248 deforms the cover layer 242 and the adhesive layer 244 towards the recessed channel 234. FIG. 7*a* illustrates a top view of the substrate layer portion 222 when the valve 226 is in the first valve closing condition. In FIG. 7*a*, as well as in FIGS. 8*a*-11*a*, the fluid manipulation valve assembly 220 is illustrated without the elastically deformable cover such that the features of the substrate layer 222 can be seen without looking through the elastically deformable cover.

Figure 8A:
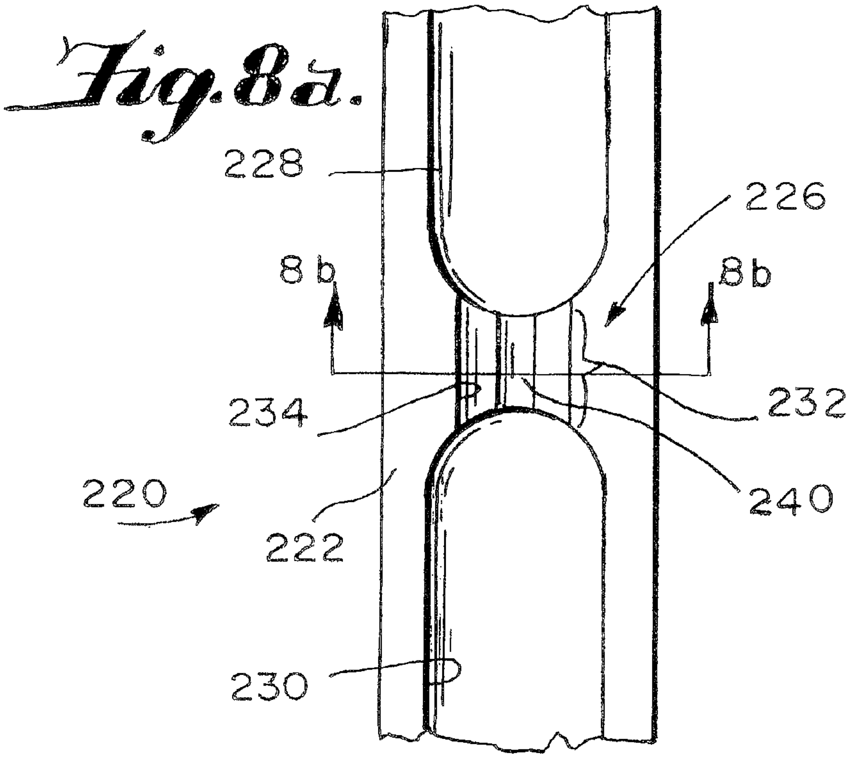
FIG. 8*a* is a top view of a fluid manipulation valve assembly that can be used according to various embodiments, in a second stage of actuation of the valve assembly.
Figure 8B:
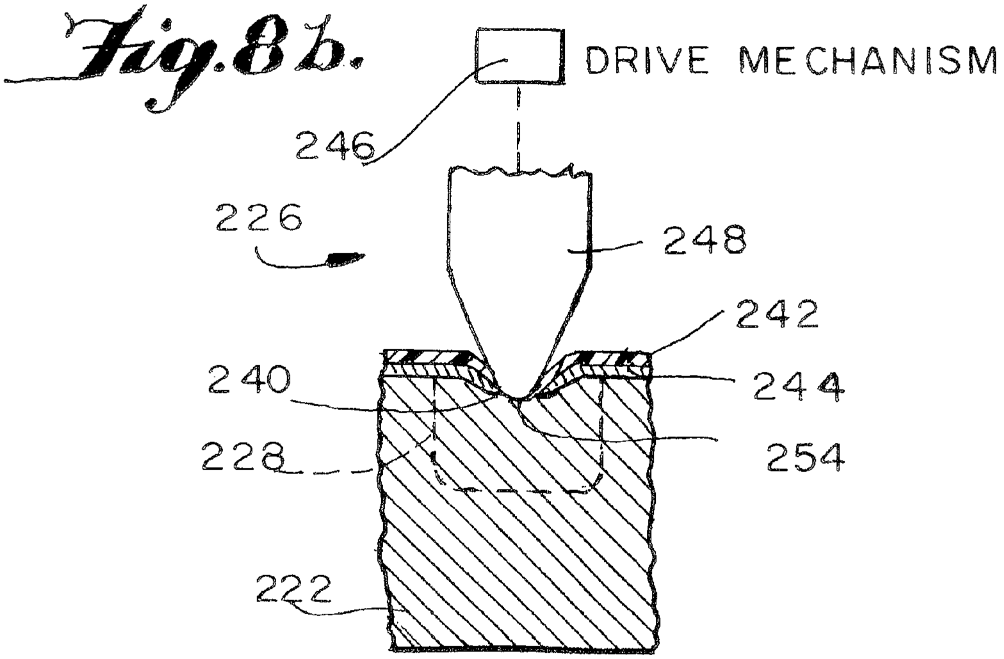
FIG. 8*b* is a cross-sectional side view of the fluid manipulation valve assembly shown in FIG. 8*a*, taken along line 8*b*-8*b* of FIG. 8*a*, and shown in a further deformed state corresponding to the second stage of actuation.
Figure 9A:
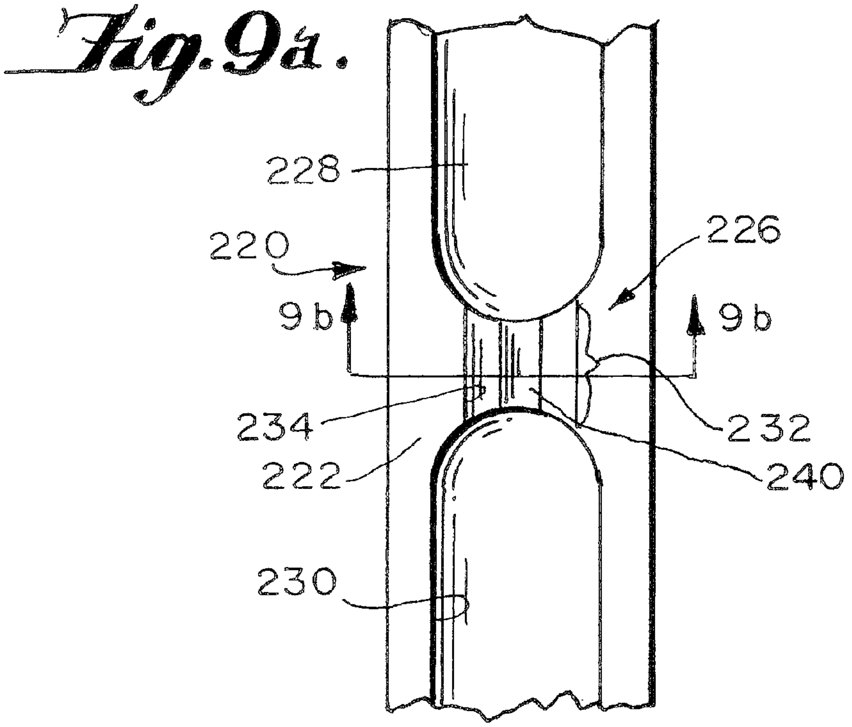
FIG. 9*a* is a top view of a fluid manipulation valve assembly that can be used according to various embodiments, in a third stage of actuation of the valve assembly.
Figure 9B:
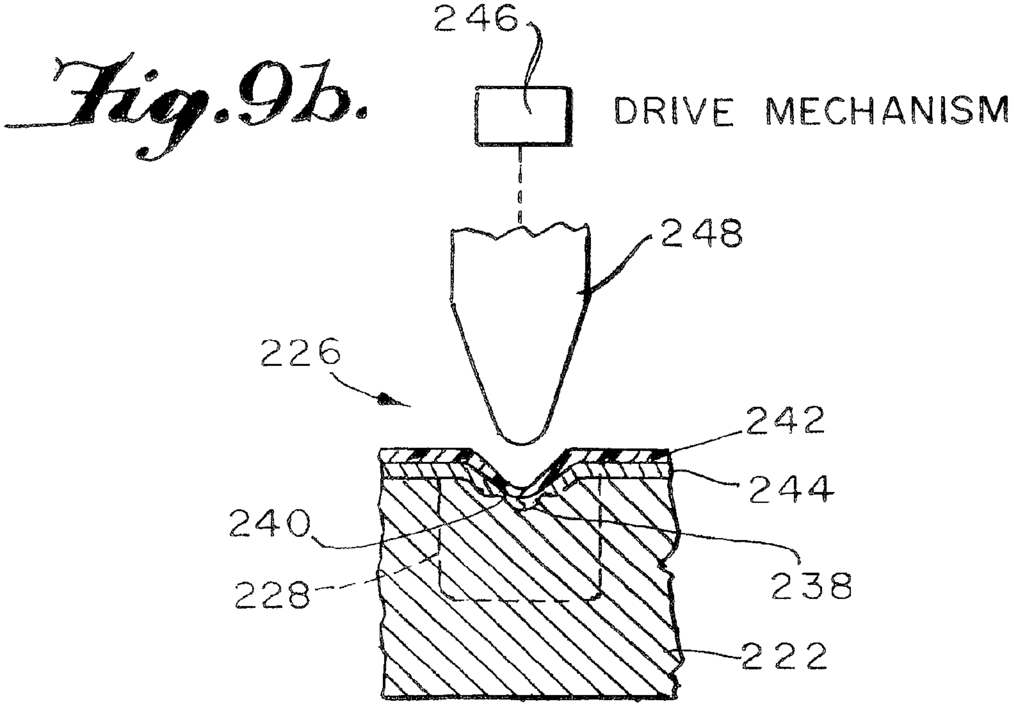
FIG. 9*b* is a cross-sectional side view of the fluid manipulation valve assembly shown in FIG. 9*a*, taken along line 9*b*-9*b* of FIG. 9*a*, and corresponding to the third stage of actuation.

According to various embodiments, the closed valve 226 of the fluid manipulation valve assembly 220 is capable of being re-opened, and then re-closed. FIGS. 7*b*, 8*b* and 9*b* illustrate the sequence of a procedure for re-opening the valve 226 starting from the first closed valve condition, according to various embodiments.

As can be seen in FIG. 8*b*, in a first re-opening step, the drive mechanism 246 can further actuate the first deformer 248 such that the contact surface 254 of the first deformer 248 deforms the cover layer 242 into the intermediate wall portion 232 of the substrate layer 222, thereby also displacing adhesive in a direction away from the first deformer 248. As a result, the intermediate wall 232 can be deformed by the deforming force of the first deformer 248 to form a deformation channel 240 in the substrate layer 222. With respect to FIG. 8*b*, the first deformer 248 can press the elastically deformable cover layer 242 through the adhesive layer 244 such that substantially none of the adhesive can be present between the cover layer 242 and the deformation channel 240. As a result, as discussed below with reference to FIG. 9*b*, when the first deformer 248 is removed from being in contact with the valve 226, the cover layer 242 can elastically rebound, forming a fluid communication opening 238.

FIG. 9*b* illustrates the second re-opening step which re-establishes the fluid communication between the recesses 228, 230. In the second re-opening step, the first deformer 248 is withdrawn from contacting the valve 226, thereby allowing the elastically deformable cover layer 242 to recover or rebound in a direction away from the deformation channel 240 formed in the intermediate wall 232. The inelastically deformable material of the intermediate wall 232 remains deformed, or remains deformed for a particular period of time, after the first deformer 248 is withdrawn. Upon recovering or rebounding, a portion of the elastically deformable cover layer 242 adjacent the deformation channel 240 of the intermediate wall 232, is spaced a set distance from the deformation channel 240 such that a fluid communication opening 238 can be formed. Thus, the fluid communication between the first and second recesses 228, 230 can be re-established.

Figure 10A:
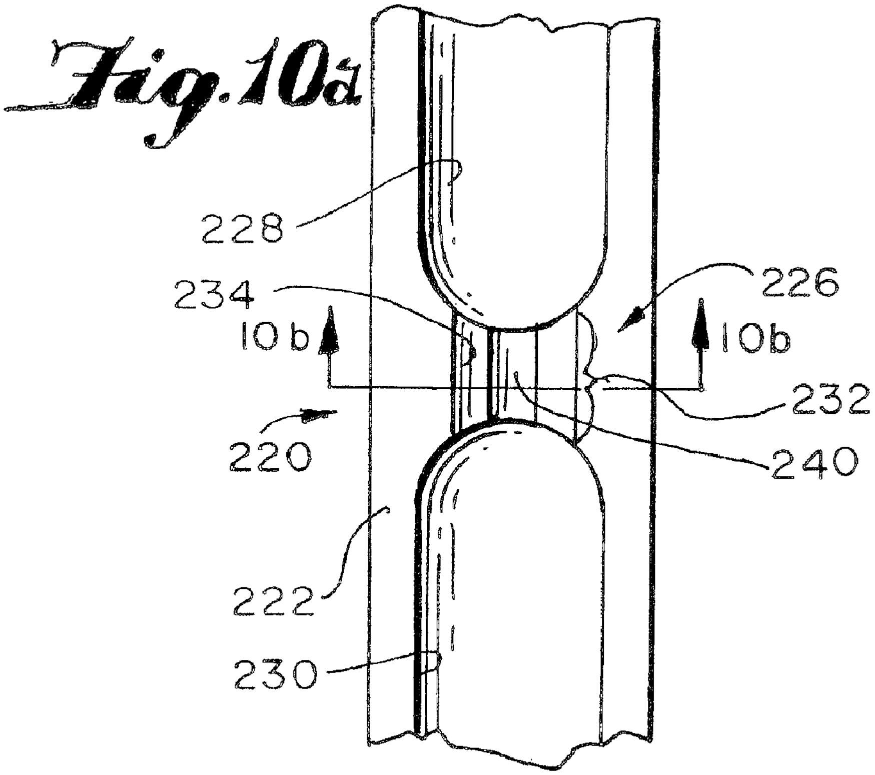
FIG. 10*a* is a top view of a fluid manipulation valve assembly that can be used according to various embodiments and prior to a fourth stage of actuation of the valve assembly.
Figure 10B:
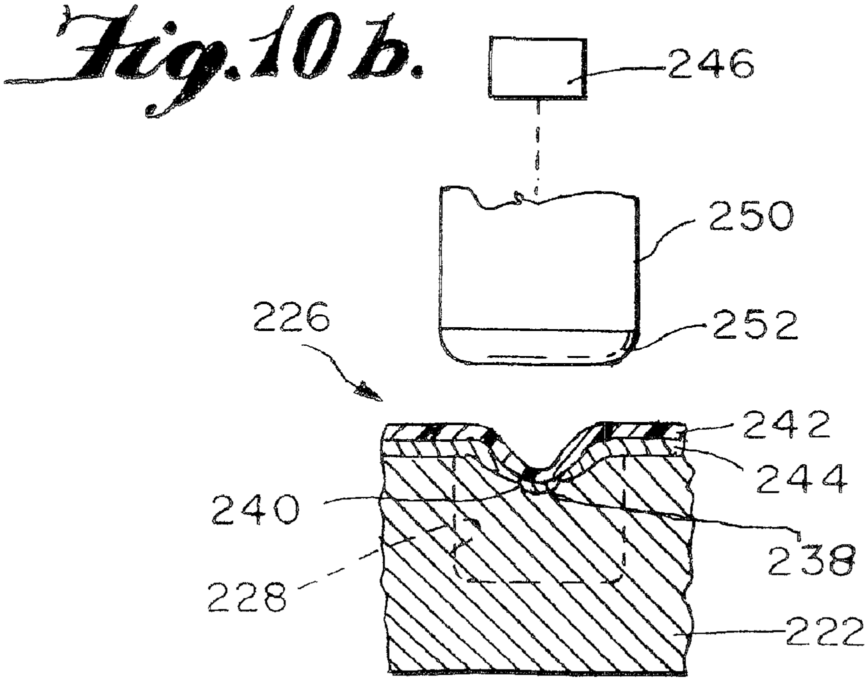
FIG. 10*b* is a cross-sectional side view of the fluid manipulation valve assembly shown in FIG. 10*a*, taken along line 10*b*-10*b* of FIG. 10*a*, and shown with the elastically deformable cover partially rebounded from the substrate layer.
Figure 11A:
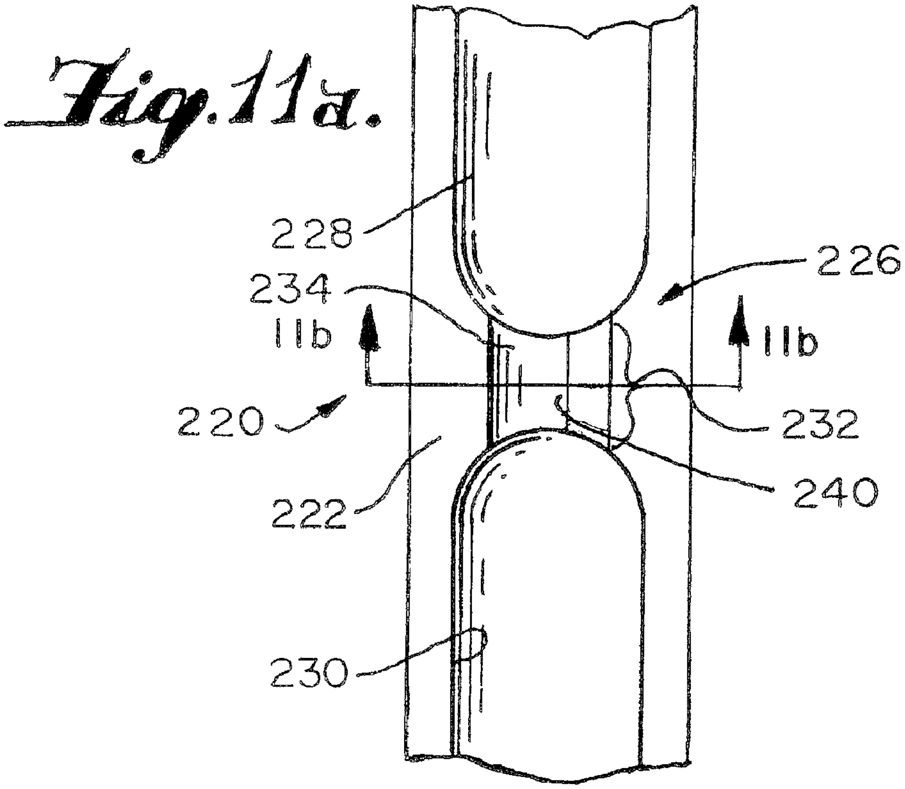
FIG. 11*a* is a top view of the substrate layer of the fluid manipulation valve assembly according to various embodiments, shown with the elastically deformable cover removed for clarity and in a fourth stage of actuation of the valve assembly.
Figure 11B:
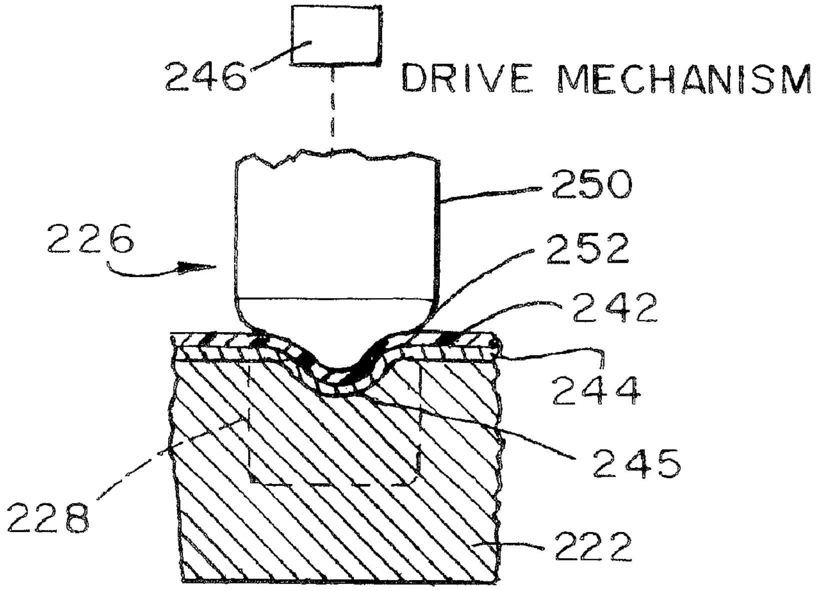
FIG. 11*b* is a cross-sectional side view of the fluid manipulation valve assembly shown in FIG. 11*a*, taken along line 11*b*-11*b* of FIG. 11*a*, and shown with the elastically deformable cover in a further deformed state, whereby the valve assembly has been re-closed in accordance with a fourth stage of actuation.

FIGS. 9*b*, 10*b* and 11*b* sequentially illustrate a procedure for re-closing the valve 226 starting from the condition that fluid communication between the first and second recesses 228, 230 has been re-established by way of the formation of the fluid communication opening 238. As can be seen in FIG. 10*b*, in a first re-closing step, the drive mechanism 246 can drive a second deformer 250 in a direction towards and into contact with the elastically deformable cover layer 242 of the open valve 226. The second deformer 250 can include a contact pad 252 or similar compliant device attached at an actuating end thereof.

FIG. 11*b* illustrates the second re-closing step which results in the fluid communication between the recesses 228, 230 being re-closed. In the second re-closing step, the drive mechanism 246 can force the contact pad 252 of the second deformer 250 into contact with the elastically deformable cover layer 242. When forcibly brought into contact with the cover layer 242, the contact pad 252 can mold into the shape of the depression formed by the cover layer 242, the adhesive layer 244 and the intermediate wall 232. As a result of the compliant or malleable characteristics of the pad 252, the material of the pad 252 can operate to manipulate the adhesive 245 of the adhesive layer 44 into the area of the fluid communication opening 238, thereby re-closing the valve 226.

The series of steps shown in FIGS. 6*a*-11*a* and FIGS. 11*a*-11*b* can be sequential or in any other order. For example, the valve 226 can be opened starting from an initially closed position, or the valve 226 can be closed from the initially open position shown in FIG. 10*b*.

The present teachings relate to the foregoing and other embodiments as will be apparent to those skilled in the art from consideration of the present specification and practice of the present teachings disclosed herein. It is intended that the present teachings be considered as exemplary only.

What is claimed is:

1. A method comprising:

providing a microfluidic device comprising
- a substrate,
- a fluid processing pathway formed in or on the substrate and including a pathway end comprising a loading chamber, and
- a separation chamber formed in or on the substrate and in fluid communication with the pathway end, the separation chamber comprising
  - a first input opening,
  - a second input opening,
  - an output opening, and a material separation region disposed between the second input opening and the output opening, and wherein the material separation region is disposed along the fluid processing pathway further from the pathway end of the fluid processing pathway than are the second input opening and the output opening;

providing a first material having a first density and a second material having a second density that is less than the first density, in the material separation region;

separating the first material from the second material in the material separation region; and removing the second material, without removing the first material, from the material separation region.

2. The method of claim 1, wherein the first material comprises water-insoluble colloidal rod particles.

3. The method of claim 1, wherein the first material comprises purification particles.

4. The method of claim 1, wherein the material separation region comprises a U-shaped channel.

5. The method of claim 1, further comprising mixing a sample with the first material in the material separation region to form a product.

6. The method of claim 5, further comprising removing the product from the material separation region.

7. The method of claim 5, wherein the mixing comprises ultrasonically mixing together the sample and the first material to form a product.

8. The method of claim 1, wherein the separating comprises spinning the microfluidic device.

9. The method of claim 1, wherein the second material comprises a carrier and removing the second material comprises causing a pressure differential across the material separation region.

10. The method of claim 6, wherein removing the product comprises causing a pressure differential across the material separation region.

11. The method of claim 1, wherein the denser first material comprises optically detectable markers, and the method further comprises irradiating the optically detectable markers with electromagnetic radiation.

12. The method of claim 11, further comprising detecting emission beams emitted from the optically detectable markers.

13. The method of claim 1, further comprising examining the denser first material with an electron microscope.

14. The method of claim 1, wherein the denser first material is water-insoluble at 25° C. and the denser first material and the second material together comprise a suspension, a mixture, an emulsion, or a combination thereof.

15. The method of claim 5, wherein the mixing comprises providing at least one air bubble in the material-trapping region.

16. The method of claim 1, wherein one of the first material and the second material is insoluble in the other.

17. The method of claim 1, wherein the first material is a nanoparticle.

* * * * *